(12) United States Patent
Simanzhenkov et al.

(10) Patent No.: US 10,647,635 B2
(45) Date of Patent: May 12, 2020

(54) CONTROLLING CARBON DIOXIDE OUTPUT FROM AN ODH PROCESS

(71) Applicant: NOVA Chemicals (International) S.A., Fribourg (CH)

(72) Inventors: Vasily Simanzhenkov, Calgary (CA); Shahin Goodarznia, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 104 days.

(21) Appl. No.: 16/164,849

(22) Filed: Oct. 19, 2018

(65) Prior Publication Data

US 2019/0135715 A1    May 9, 2019

Related U.S. Application Data

(60) Provisional application No. 62/581,864, filed on Nov. 6, 2017.

(51) Int. Cl.
| | |
|---|---|
| *C07C 5/333* | (2006.01) |
| *C07C 5/48* | (2006.01) |
| *C07C 5/42* | (2006.01) |
| *B01J 27/057* | (2006.01) |

(52) U.S. Cl.
CPC ......... *C07C 5/3337* (2013.01); *B01J 27/0576* (2013.01); *C07C 5/42* (2013.01); *C07C 5/48* (2013.01); *C07C 2523/20* (2013.01); *C07C 2523/22* (2013.01); *C07C 2523/28* (2013.01); *C07C 2523/648* (2013.01); *C07C 2523/652* (2013.01); *C07C 2523/656* (2013.01); *C07C 2527/057* (2013.01)

(58) Field of Classification Search
CPC .................................. C07C 5/42; C07C 5/48
USPC ......................................... 585/501, 654, 658
See application file for complete search history.

(56) References Cited

U.S. PATENT DOCUMENTS

| | | |
|---|---|---|
| 2,604,495 A | 7/1952 | Erkko |
| 3,420,911 A | 1/1969 | Woskow et al. |
| 3,420,912 A | 1/1969 | Woskow et al. |

(Continued)

OTHER PUBLICATIONS

Liu, Licheng; Jiang, Hongtao; Liu, Haitao and Li, Huiquan; Recent Advances on the Catalysts for Activation of CO2 in Several Typical Processes, Activation of Carbon Dioxide; Copyright 2013 Elsevier B.V.; Chapter 7, pp. 189-222.

*Primary Examiner* — Ali Z Fadhel
(74) *Attorney, Agent, or Firm* — Julie L. Heinrich

(57) ABSTRACT

In some embodiments provided herein are processes for controlling carbon dioxide output levels coming from an oxidative dehydrogenation (ODH) process. Carbon dioxide output from an ODH process includes that produced in the ODH reaction and carry over when carbon dioxide is used as an inert diluent. Under certain circumstances carbon dioxide can also be consumed in the ODH process by acting as an oxidizing agent. By varying the amount of steam introduced into the ODH process an operator may alter the degree to which carbon dioxide acts as an oxidizing agent. This in turn allows a level of control in the degree to which carbon dioxide is consumed in the process, effecting overall carbon dioxide output. Minimizing the carbon dioxide output provides an opportunity to limit or eliminate the requirement for release of carbon dioxide into the atmosphere.

19 Claims, 1 Drawing Sheet

(56) References Cited

U.S. PATENT DOCUMENTS

| | | | | |
|---|---|---|---|---|
| 3,709,951 | A | * | 1/1973 | Hutson, Jr. et al. ...... C07C 5/48 585/501 |
| 4,596,787 | A | | 6/1986 | Manyik et al. |
| 5,105,045 | A | * | 4/1992 | Kimble .................. B01J 27/32 585/400 |
| 6,891,075 | B2 | | 5/2005 | Liu |
| 7,319,179 | B2 | | 1/2008 | Lopez Nieto et al. |
| 7,767,770 | B2 | | 8/2010 | Han et al. |
| 2002/0055664 | A1 | * | 5/2002 | Liu .......................... B01J 23/76 585/658 |
| 2004/0097774 | A1 | * | 5/2004 | Hall .......................... B01J 8/02 585/658 |
| 2006/0135838 | A1 | * | 6/2006 | Bagherzadeh ........... B01J 21/06 585/660 |
| 2008/0177117 | A1 | * | 7/2008 | Benderly .................. C07C 5/48 585/324 |
| 2009/0240094 | A1 | * | 9/2009 | Crone .................. C07C 5/3337 585/655 |
| 2018/0154341 | A1 | * | 6/2018 | Goyal ....................... C07C 5/48 |

* cited by examiner

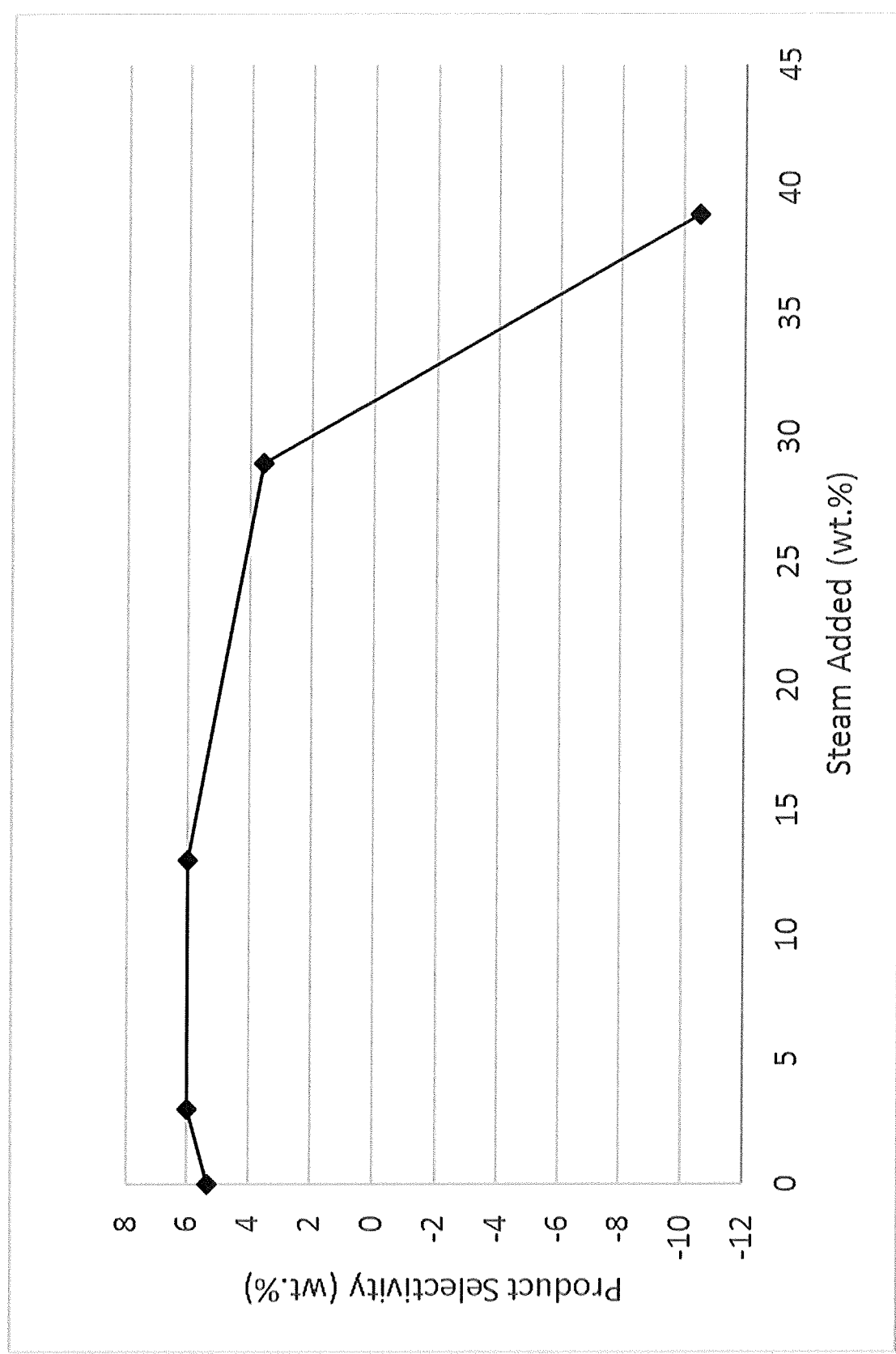

CONTROLLING CARBON DIOXIDE OUTPUT FROM AN ODH PROCESS

The present disclosure relates generally to oxidative dehydrogenation (ODH) of lower alkanes into corresponding alkenes. In some embodiments, the present disclosure relates to controlling the carbon dioxide output levels from an ODH process.

Olefins like ethylene, propylene, and butylene, are basic building blocks for a variety of commercially valuable polymers. Since naturally occurring sources of olefins do not exist in commercial quantities polymer producers rely on methods for converting the more abundant lower alkanes into olefins. The method of choice for today's commercial scale producers is steam cracking, a highly endothermic process where steam-diluted alkanes are subjected very briefly to a temperature of at least 700° C. The fuel demand to produce the required temperatures and the need for equipment that can withstand that temperature add significantly to the overall cost. Also, the high temperature promotes the formation of coke which accumulates within the system, resulting in the need for costly periodic reactor shut-down for maintenance and coke removal.

Oxidative dehydrogenation (ODH) is an alternative to steam cracking that is exothermic and produces little or no coke. In ODH a lower alkane, such as ethane, is mixed with oxygen in the presence of a catalyst and optionally an inert diluent, such as carbon dioxide or nitrogen, in some embodiments at temperatures as low as 300° C., to produce the corresponding alkene. In some embodiments, and unfortunately, various other oxidation products, most notably carbon dioxide and acetic acid may also be produced in this process. In some embodiments ODH suffers from lower conversion rates when compared to steam cracking, a fact that when combined with lower selectivity and the risk of thermal explosion due to mixing of a hydrocarbon with oxygen, has prevented ODH from achieving widespread commercial implementation.

The concept of ODH has been known since at least the late 1960's. Since that time considerable effort has been expended on improving the process, including improving catalyst efficiency and selectivity. This has resulted in numerous patents for various catalyst types including carbon molecular sieves, metal phosphates, and most notably mixed metal oxides. Early catalyst U.S. patents assigned to Petro-Tex Chemicals taught the use of ferrites in the oxidative dehydrogenation of organic compounds. The ferrites are introduced into a dehydrogenation zone containing the organic compound and an oxidant for a short period, then to a regeneration zone for reoxidation, and then fed back to the dehydrogenation zone for another cycle.

The preparation of a supported catalyst useful for low-temperature oxidative dehydrogenation of ethane to ethylene has been disclosed by Union Carbide Corporation. The catalyst is prepared by (a) preparing a precursor solution having soluble and insoluble portions of metal compounds, (b) separating the soluble portion, (c) impregnating a catalyst support with the soluble portion and (d) activating the impregnated support to obtain the catalyst. The calcined catalyst has the composition $$Mo_aV_bNb_cSb_dX_e$$

wherein X is nothing or Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U, Mn and/or W; a is 0.5-0.9; b is 0.1-0.4; c is 0.001-0.2; d is 0.001-0.1; and e is 0.001-0.1 when X is an element.

Symyx Technologies, Inc. teaches a catalyst for the oxidative dehydrogenation of a paraffin (alkane) such as ethane. The gaseous feedstock comprises at least the alkane and oxygen, but may also include diluents (such as, argon, nitrogen, etc.) or other components (such as, steam or carbon dioxide). The dehydrogenation catalyst comprises at least about 2 weight % of NiO and a broad range of other elements, preferably, Nb, Ta, and Co. The claims required a selectivity for ethylene of at least 70%, with conversions over 10%.

Mo—V—Te—Nb—O oxide catalysts that provided an ethane conversion of 50-70% and selectivity to ethylene up to 95% (at 38% conversion) at 360 to 400° C. have been disclosed. The catalysts have the empirical formula $MoTe_hV_iNb_jA_kO_x$, where A is a fifth modifying element. The catalyst is a calcined mixed oxide (at least of Mo, Te, V and Nb), optionally supported on: (i) silica, alumina and/or titania, preferably silica at 20 to 70 wt. % of the total supported catalyst or (ii) silicon carbide. The supported catalyst is prepared by conventional methods of precipitation from solutions, drying the precipitate and then calcining.

The oxidizing agent in the ODH process is typically the oxygen added with the lower alkane. However, it is known that carbon dioxide may also act as an oxidizing agent. Liu, et. al., review the literature on $CO_2$ as an oxidizing agent in the oxidative dehydrogenation of alkanes in New and Future Developments in Catalysis, Elsevier, 189-222 (2013), "Chapter 7—Recent Advances on the Catalysts for Activation of $CO_2$ in Several Typical Processes". Studies have shown that $CO_2$ can act as mild oxidant in ODH reactions, which can inhibit deep oxidation of the reaction products and also provides a mechanism for using $CO_2$ as a resource. For ODH of ethane into ethylene, catalyst types include active metal and oxides, supported on $SiO_2$, $ZrO_2$, $Al_2O_3$ or $TiO_2$, combinations of which show varying conversion rates and selectivity to ethylene.

Hercules Powder Company has a process for dehydrogenating ethane to produce ethylene by mixing carbon dioxide and ethane in the presence of iron oxide catalyst at temperatures between 750° C. and 950° C. They showed conversion rates of ethane to ethylene of between 34% and 68.7%, depending upon the molar ratio of carbon dioxide to ethane added to the reactor and the catalyst composition.

At least Rohm and Haas Company has taught a method for producing a mixture of ethylene and carbon monoxide by contacting ethane and carbon dioxide with a mixed valent catalyst. Reactions are conducted in the absence of elemental oxygen at temperatures of at least 550° C., and produce a mixture of ethylene and carbon monoxide that can be used as feedstock for other processes, such as a process for producing methacrylic acid esters.

We have discovered that the degree to which carbon dioxide, either produced during the ODH process or added as a diluent, acts as an oxidizing agent can be manipulated so as to control the output of carbon dioxide from the process to a desired level. Using the methods described herein a user may choose to operate in carbon dioxide neutral conditions such that surplus carbon dioxide need not be flared or released into the atmosphere.

DESCRIPTION OF THE DRAWINGS

The FIGURE is a graphical representation of the results from Table 1.

Disclosed herein are methods for controlling the carbon dioxide output from an ODH process, which methods comprises introducing, into at least one ODH reactor a gas mixture of a lower alkane, oxygen and carbon dioxide, under conditions that allow production of the corresponding alkene and smaller amounts of various by-products. For multiple ODH reactors, each reactor contains the same or different ODH catalyst, provided at least one ODH catalyst is capable of using carbon dioxide as an oxidizing agent. In some embodiments steam or other inert diluents may also be introduced into the reactor as part of the gas mixture. In some embodiments the amount of carbon dioxide leaving the reactor is subsequently monitored. If the amount of carbon dioxide output is below a desired level then the amount of steam introduced into the reactor can be increased. If the amount of carbon dioxide output is above the desired level then the amount of steam introduced into the reactor can be decreased. Alternatively, the volumetric ratio of oxygen:lower alkane added to the at least one ODH reactor can be increased to decrease the carbon dioxide output, or the volumetric ratio of oxygen:lower alkane added to the at least one ODH reactor can be decreased to increase the carbon dioxide output.

In some embodiments the lower alkane is ethane, and the corresponding alkene is ethylene.

In further embodiments, at least one ODH reactor is a fixed bed reactor. In some embodiments at least one ODH reactor is a fixed bed reactor that includes heat dissipative particles within the fixed bed. In some embodiments the heat dissipative particles have a thermal conductivity that is greater than the catalyst. In alternative embodiments, at least one ODH reactor is a fluidized bed reactor.

In some embodiments at least one ODH catalyst is a mixed metal oxide catalyst. In further embodiments, at least one ODH catalyst is a mixed metal oxide of the formula: $Mo_aV_bTe_cNb_dPd_eO_f$, wherein a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to satisfy the valence state of the catalyst.

This disclosure relates to oxidative dehydrogenation (ODH) of lower alkanes into corresponding alkenes. Lower alkanes are intended to include saturated hydrocarbons with from 2 to 4 carbons, and the corresponding alkene includes hydrocarbons with the same number of carbons, but with a single double carbon to carbon bond. While any of the lower alkanes can be converted to their corresponding alkenes using the methods disclosed herein, the present disclosure focuses on the ODH of ethane, producing its corresponding alkene, ethylene.

The ODH Process

ODH of lower alkanes comprises contacting a mixture of a lower alkane and oxygen in an ODH reactor with an ODH catalyst under conditions that promote oxidation of the lower alkane into its corresponding alkene. Conditions within the reactor are controlled by the operator and include, but are not limited to, parameters such as temperature, pressure, and flow rate. Conditions will vary and can be optimized for a particular lower alkane, or for a specific catalyst, or whether an inert diluent is used in the mixing of the reactants.

Use of an ODH reactor for performing an ODH process consistent with the disclosure falls within the knowledge of the person skilled in the art. For best results, the oxidative dehydrogenation of a lower alkane may be conducted at temperatures from 300° C. to 450° C., or from 300° C. to 425° C., or from 330° C. to 400° C., at pressures from 0.5 to 100 psi (3.447 to 689.47 kPa), or from 15 to 50 psi (103.4 to 344.73 kPa), and the residence time of the lower alkane in the reactor may be from 0.002 to 30 seconds, or from 1 to 10 seconds. While the ODH process is likely to occur at temperatures less than 300, in some embodiments, it is not expected to be efficient or commercially viable.

In some embodiments the process has a selectivity for the corresponding alkene (ethylene in the case of ethane ODH) of greater than 85%, or greater than 90%. The flow of reactants and inert diluent can be described in any number of ways known in the art. In some embodiments, flow is described and measured in relation to the volume of all feed gases (reactants and diluent) that pass over the volume of the active catalyst bed in one hour, or gas hourly space velocity (GHSV). The GHSV can range from 500 to 30000 $h^{-1}$, or greater than 1000 $h^{-1}$ or greater than 1000 $h^{-1}$ but up to 30000 $h^{-1}$. The flow rate can also be measured as weight hourly space velocity (WHSV), which describes the flow in terms of the weight, as opposed to volume, of the gases that flow over the weight of the active catalyst per hour. In calculating WHSV the weight of the gases may include only the reactants but may also include diluents added to the gas mixture. When including the weight of diluents, when used, the WHSV may range from 0.5 $h^{-1}$ to 50 $h^{-1}$, preferably from 1.0 to 25.0 $h^{-1}$.

The flow of gases through the reactor may also be described as the linear velocity of the gas stream (m/s), which is defined in the art as the flow rate of the gas stream/cross-sectional surface area of the reactor/void fraction of the catalyst bed. The flow rate generally means the total of the flow rates of all the gases entering the reactor and is measured where the oxygen and alkane first contact the catalyst and at the temperature and pressure at that point. The cross-section of the reactor is also measured at the entrance of the catalyst bed. The void fraction of the catalyst bed is defined as the volume of voids in the catalyst bed/total volume of the catalyst bed. The volume of voids refers to the voids between catalyst particles and does not include the volume of pores inside the catalyst particles. The linear velocity can range from 5 cm/sec to 1500 cm/sec, preferably from 10 cm/sec to 500 cm/sec.

The space-time yield of corresponding alkene (productivity) in g/hour per kg of the catalyst should be at least 100 or above, or greater than 500, or greater than 1500, up to a maximum of 2000. at 350 to 400° C. In some embodiments the productivity of the catalyst will increase with increasing temperature until the selectivity is sacrificed.

ODH Catalyst

Any of the ODH catalysts known in the art are suitable for use with the methods disclosed herein. When choosing a catalyst, a skilled user would appreciate that catalysts can vary with respective to selectivity and activity. For some embodiments of ODH of ethane, mixed metal oxides are the catalyst of choice as they can provide high selectivity to ethylene without significant loss in activity. Example catalysts are those of the formula:

$Mo_aV_bTe_cNb_dPd_eO_f$ wherein a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to satisfy the valence state of the catalyst.

ODH Reactor

Any of the known reactor types applicable for the ODH of lower alkanes may be used with the methods disclosed herein. In some embodiments the methods may be used with conventional fixed bed reactors. In a typical fixed bed reactor reactants are introduced into the reactor at one end, flow past an immobilized catalyst, products are formed and leave at the other end of the reactor. Designing a fixed bed reactor suitable for the methods disclosed herein can follow techniques known for reactors of this type. A person skilled in the art would know which features are required with respect to shape and dimensions, inputs for reactants, outputs for products, temperature and pressure control, and means for immobilizing the catalyst.

Also contemplated are the use of inert non-catalytic heat dissipative particles within one or more of the ODH reactors, in some embodiments. In some embodiments, the heat dissipative particles are present within the bed and comprise one or more non catalytic inert particulates having a melting point at least 30° C. in some embodiments, at least 250° C. in further embodiments, and in further embodiments at least 500° C. and up to a maximum of 600° C. above the temperature upper control limit for the reaction, 600° C., a particle size in range of 0.5 to 75 mm, in some embodiments 0.5 to 15 mm, in further embodiments in range of 0.5 to 8 mm, in further embodiments in the range of 0.5 to 5 mm and a thermal conductivity of greater than 30 W/mK (watts/meter Kelvin) within the reaction temperature control limits. In some embodiments the particulates are metals alloys and compounds having a thermal conductivity of greater than 50 W/mK (watts/meter Kelvin) within the reaction temperature control limits. Some suitable metals include silver, copper, gold, aluminum, steel, stainless steel, molybdenum, and tungsten.

The heat dissipative particles may have a particle size typically from about 1 to 15 mm. In some embodiments the particle size may be from about 1 mm to about 8 mm. The heat dissipative particles may be added to the fixed bed in an amount from 5 to 95 wt. %, in some embodiments 30 to 70 wt. %, in other embodiments 45 to 60 wt. % based on the entire weight of the fixed bed. The particles are employed to potentially improve cooling homogeneity and reduction of hot spots in the fixed bed by transferring heat directly to the walls of the reactor.

Also contemplated is the use of a fluidized bed reactor, where typically, the catalyst is supported by a porous structure, or distributor plate, located near a bottom end of the reactor and reactants flow through at a velocity sufficient to fluidize the bed (e.g. the catalyst rises and begins to swirl around in a fluidized manner). The reactants are converted to products upon contact with the fluidized catalyst and subsequently removed from the upper end of the reactor. Design considerations include shape of the reactor and distributor plate, input and output, and temperature and pressure control, all of which would fall under knowledge of the person skilled in the art.

The present disclosure also contemplates using a combination of both fixed bed and fluidized bed reactors, each with the same or different catalyst. The multiple reactors may be in series, or parallel configuration, design of which falls within the knowledge of the worker skilled in the art.

Flammability Limits

Safety of the process is a primary concern. For that reason, mixtures of a lower alkane with oxygen should, in some embodiments, comprise ratios that fall outside of the flammability envelope. In some embodiments a ratio of alkane to oxygen may fall outside the upper flammability envelope. In this instance the percentage of oxygen in the mixture is less than 30%, or less than 25%, or less than 20%.

In embodiments with higher oxygen percentages alkane percentages may be adjusted to keep the mixture outside of the flammability envelope. While a person skilled in the art would be able to determine an appropriate level it is recommended that the percentage of alkane is less 40%. For instance, in an example where the mixture of gases prior to ODH comprises 20% oxygen and 40% alkane, the balance must be made up with an inert diluent, such as one or more of nitrogen, carbon dioxide, and steam. In some embodiments the inert diluent should exist in the gaseous state in the conditions within the reactor and should not increase the flammability of the hydrocarbon added to the reactor, characteristics that a skilled worker would understand when deciding on which inert diluent to employ. Inert diluent can be added to either of the lower alkane containing gas or the oxygen containing gas prior to entering the ODH reactor or may be added directly into the ODH reactor.

In some embodiments mixtures that fall within the flammability envelope may be employed, for example, in instances where the mixture exists in conditions that prevent propagation of an explosive event. That is, the flammable mixture is created within a medium where ignition is immediately quenched. For example, a user may design a reactor where oxygen and the lower alkane are mixed at a point where they are surrounded by flame arresting material. Any ignition would be quenched by the surrounding material. Flame arresting materials include but are not limited to metallic or ceramic components, such as stainless steel walls or ceramic supports. In some embodiments oxygen and lower alkane can be mixed at a low temperature, where an ignition event would not lead to an explosion, then introduced into the reactor before increasing the temperature. The flammable conditions don't exist until the mixture is surrounded by the flame arrestor material inside of the reactor.

Carbon Dioxide Output

Carbon dioxide can be produced in the ODH reaction as a by-product of oxidation of the lower alkane. Carbon dioxide can also be added into the ODH reactor when used as an inert diluent. Conversely, carbon dioxide may be consumed when it acts as an oxidant for the dehydrogenation reaction. The carbon dioxide output is therefore a function of the amount of carbon dioxide added and produced minus that consumed in the oxidative process. In some embodiments, the disclosed methods control the degree to which carbon dioxide acts as an oxidizing agent so as to impact the overall carbon dioxide output coming off the ODH reactor.

Measuring the amount of carbon dioxide coming off the ODH reactor can be done using any means known in the art. For example, one or more detectors such as GC, IR, or Raman detectors, are situated immediately downstream of the reactor to measure the carbon dioxide output. While not required, the output of other components may also be measured. These include but are not limited to the amounts of ethylene, unreacted ethane and oxygen, and by-products such as acetic acid. Also, it should be noted that depending on the chosen metric for carbon dioxide output, the output levels of the other components, for example ethane, may actually be required.

Carbon dioxide output can be stated using any metric commonly used in the art. For example, the carbon dioxide output can be described in terms of mass flow rate (g/min) or volumetric flow rate ($cm^3$/min). In some embodiments, normalized selectivity can be used to assess the degree to which carbon dioxide is produced or consumed. In that instance the net mass flow rate of $CO_2$—the difference between the mass flow rate of $CO_2$ entering and leaving the ODH reactor—is normalized to the conversion of ethane, in essence describing what fraction of ethane is converted into carbon dioxide as opposed to ethylene, or other by-products such as acetic acid. A carbon selectivity of 0 indicates that the amount of carbon dioxide entering the reactor is the same as the carbon dioxide output. In other words, the process is carbon dioxide neutral. A positive carbon dioxide selectivity alerts a user that carbon dioxide is being produced, and that any oxidation of carbon dioxide that is occurring is insufficient to offset that production, resulting in the process being carbon dioxide positive.

When output of carbon dioxide, or other components produced such as acetic acid and carbon monoxide, are described in terms of normalized product selectivity, the calculation is performed according to the formula:

$$\text{Selectivity (wt \%)} = \frac{\dfrac{\text{Net mass flow rate of } X \text{ (g }X/\text{min)}}{\text{Molecular weight of } X \text{ (g }X/\text{mol }X)}}{\left[\dfrac{\text{Net mass flow rate of converted } C_2H_6 \text{ (g } C_2H_6/\text{min)}}{\text{Molecular weight of } C_2H_6 \text{ (g } C_2H_6/\text{mol } C_2H_6)}\right] * \dfrac{\text{Mol. Equiv. of } X}{\text{mol } C_2H_6}$$

where X is the product that is being assessed, the net mass flow rate refers to flow in g/min for X or ethane entering the reactor minus the flow rate exiting the reactor, and molar equivalent (Mol. Equiv.) refers to the amount of X, in moles, that reacts completely with one mole of ethane. Selectivity is referred to as a wt. % despite the fact the calculation results in converting wt % to a molar percentage because weight flow rate is the measurement that is used in the calculation.

One potential advantage of the present disclosure is the possibility of carbon dioxide negative process. In this instance, carbon dioxide is oxidized at a higher rate than it is produced and shows a negative carbon selectivity. The ODH process may be producing carbon dioxide, but the degree to which carbon dioxide is consumed while acting as an oxidizing agent offsets any production that is occurring. Many industrial processes, in addition to ODH, produce carbon dioxide which must be captured or flared where it contributes to the emission of greenhouse gases. Using a carbon dioxide negative process the excess carbon dioxide from other processes may be captured and used as the inert diluent in the ODH process under conditions where there is negative carbon selectivity. Another advantage, then, is the ability to reduce the amount of carbon dioxide produced in the ODH process in combination with other processes, such as thermal cracking. In addition, oxidation of carbon dioxide is endothermic and by increasing the degree to which carbon dioxide acts as an oxidizing agent, heat produced from ODH of ethane is partially offset by oxidation of carbon dioxide, reducing the degree to which heat must be removed from the reactor. In some embodiments, when acting as an oxidizing agent, carbon dioxide can produce carbon monoxide, which can be captured and used as an intermediate in production of other chemical products, such as methanol or formic acid.

Addition of Steam

The amount of steam added to the ODH process affects the degree to which carbon dioxide acts as an oxidizing agent. In some embodiments steam may be added directly to the ODH reactor, or steam may be added to the individual reactant components—the lower alkane, oxygen, or inert diluent—or combinations thereof, and subsequently introduced into the ODH reactor along with one or more of the reactant components. Alternatively, steam may be added indirectly as water mixed with either the lower alkane, oxygen or inert diluent, or a combination thereof, with the resulting mixture being preheated before entering the reactor. When adding steam indirectly as water, the preheating process should increase the temperature, so that the water is entirely converted to steam before entering the reactor.

Increasing the amount of steam added to a reactor increases the degree to which carbon dioxide acts as an oxidizing agent. Decreasing the amount of steam added to the reactor decreases the degree to which carbon dioxide acts as an oxidizing agent. In some embodiments a user monitors the carbon dioxide output and compares it to a predetermined target carbon dioxide output. If the carbon dioxide output is above the target a user can then increase the amount of steam added to the ODH process. If the carbon dioxide output is below the target a user can decrease the amount of steam added to the ODH process, provided steam has been added. Setting a target carbon dioxide output level is dependent on the requirements for the user. In some embodiments increasing the steam added will have the added effect of increasing the amount of acetic acid and other by-products produced in the process. A user that is ill equipped to separate out larger amounts of acetic acid from the output of the ODH may prefer to reduce steam levels to a minimum, while a user that desires a process that consumes carbon dioxide may prefer to maximize the amount of steam that can be added. In some embodiments, the amount of steam added to one or more reactors is up to 60 wt. %. It should be noted that using wt. % to describe the amount of steam, or other components, added as part of the feed is a true wt. %, meaning it is the mass flow rate of the component divided by the total mass flow of all feed components multiplied by 100. This is different than the use of wt. % to describe product selectivity.

The effect of adding steam on the carbon dioxide output is more pronounced at lower temperatures. For example, at temperatures ranging from 300° C. to 340° C. the carbon dioxide selectivity may change from 1 wt. % to 20 wt. %, depending upon the change in steam added to the reaction. On the other hand, at higher temperatures, ranging from 350° C. to 425° C., the change in carbon dioxide selectivity may range from 0.25 wt. % to 1.5%.

In some embodiments, where reaction temperatures are less than 340° C., changing the amount of steam added to the reactor by at least 20 wt. % results in a change in carbon dioxide output, measured as normalized product selectivity, of at least 1 wt. %.

In some embodiments, where reaction temperatures are less than 340° C., and the amount of steam added to the reactor is from 0 wt. % to about 20 wt. % and is increased to from about 35 wt. % to about 60 wt. % the result is an absolute decrease in carbon dioxide output, measured as normalized product selectivity, of from 2.5 wt. % to 15 wt. %.

In some embodiments, where reaction temperatures are less than 340° C., and the amount of steam added to the reactor is from 35 wt. % to about 60 wt. % and is decreased to from about 20 wt. % to about 0 wt. % the result is an absolute increase in carbon dioxide output, measured as normalized product selectivity, of from 2.5 wt. % to 15 wt. %.

In some embodiments, where reaction temperatures are greater than 350° C., and the amount of steam added to the reactor is from about 0 wt. % to about 10 wt. % and increased to from about 40 wt. % to about 60 wt. % and results in an absolute decrease in carbon dioxide output, measured as normalized product selectivity, of from about 0.5 wt. % to 1.0 wt. %.

In some embodiments, where reaction temperatures are greater than 350° C., and the amount of steam added to the reactor is from about 40 wt. % to about 60 wt. % and decreased to from about 0 wt. % to about 10 wt. % and results in an absolute increase in carbon dioxide output, measured as normalized product selectivity, of from about 0.5 wt. % to 1.0 wt. %.

When using two or more reactors it is contemplated that a user may choose to control carbon dioxide output in only one, or less than the whole complement of reactors. For example, a user may opt to maximize carbon dioxide output of an upstream reactor so that the higher level of carbon dioxide can comprise part of the inert diluent for the subsequent reactor. In this scenario, addition of steam to the first reactor would be minimized while in the second reactor the addition of steam could be maximized to promote use of carbon dioxide as an oxidant. The carbon dioxide produced in the first reactor can act as both an inert diluent and as an oxidant in the second reactor. Maximizing carbon dioxide output upstream minimizes the amount of inert diluent that would need to be added to the stream prior to the next reactor.

There is no requirement for adding steam to an ODH process, as it is one of many alternatives for the inert diluent. For processes where no steam is added, the carbon dioxide output is maximized under the conditions used with respect to ethane, oxygen and inert diluent inputs. Decreasing the carbon dioxide output is then a matter of adding steam to the reaction until carbon dioxide output drops to the desired level. In embodiments where oxidative dehydrogenation conditions do not include addition of steam, and the carbon dioxide output is higher than the desired carbon dioxide target level, steam may be introduced into the reactor while keeping relative amounts of the main reactants and inert diluent-lower alkane, oxygen and inert diluent-added to the reactor constant, and monitoring the carbon dioxide output, increasing the amount of steam until carbon dioxide decreases to the target level.

In some embodiments, where carbon dioxide is not added as a diluent it is unlikely that a carbon dioxide negative process will occur. However, a carbon dioxide neutral process can be achieved by increasing steam added so that any carbon dioxide produced in the oxidative dehydrogenation process can then be used as an oxidizing agent such that there is no net production of carbon dioxide. Conversely, if a user desires net positive carbon dioxide output then the amount of steam added to the process can be reduced or eliminated to help maximize carbon dioxide production. As the carbon dioxide levels increase there is potential to reduce oxygen consumption, as carbon dioxide is competing as an oxidizing agent. The skilled person would understand that using steam to increase the degree to which carbon dioxide acts as an oxidizing agent can impact oxygen consumption. The implication is that a user can optimize reaction conditions with lower oxygen contributions, which may assist in keeping mixtures outside of flammability limits.

Relative Volumetric Oxygen/Ethane Ratio

The relative volumetric oxygen:ethane ratio added to the ODH process can also impact the degree to which carbon dioxide acts as an oxidizing agent. Increasing the amount of oxygen added relative to the amount of ethane added decreases the carbon dioxide selectivity. The degree which carbon dioxide selectivity changes is dependent upon the change in the relative volumetric ratio of oxygen:ethane added to the reactor and whether an inert diluent is included in the input stream. The effect is more pronounced in the absence of inert diluent, which, for safety reasons, limits the amount of oxygen added to no more than 30 vol %, or no more than 20 vol %, in the absence of diluent. It is conceivable to use a much higher vol % $O_2$, but in order to remain outside the flammability limits the corresponding amount of ethane would be restricted to levels below about 3 vol %.

The relative volumetric oxygen:ethane ratio is determined by dividing the volume % of oxygen fed to the ODH process by the volume % of ethane added. For example, a gas mixture of 20 vol % oxygen, 40 vol % inert diluent, and 40 vol % of carbon dioxide has a relative volumetric oxygen:ethane ratio of 0.5. In embodiments where there is an absence of inert diluent, the relative volumetric oxygen:ethane ratios fall between 0.1 and 0.45. In embodiments where inert diluent is present the oxygen:ethane ratio can range from 0.1 to 2.0.

Altering the ratio of oxygen:ethane can be accomplished by keeping vol % of either oxygen or ethane constant and then reducing or increasing the vol % of either oxygen or ethane and then increasing or reducing the vol % of inert diluent added to the process by an equivalent amount. In some embodiments, the vol % of oxygen added is kept constant while the ethane vol % is adjusted with corresponding adjustments to the vol % of inert diluent added. When air is used as the source of oxygen the vol % is adjusted to reflect the composition of air where oxygen is ~21 vol % and nitrogen is about ~78%. The contribution of nitrogen would be used to calculate the vol % of inert diluent added to the reaction.

In some embodiments, changing the relative volumetric ratio of oxygen:ethane can be done by reducing the vol % of either oxygen or ethane and increasing by a similar vol % the one of oxygen and ethane that was not reduced, while keeping the vol % of inert diluent added constant.

In some embodiments, the amount of oxygen added is about 20 vol. % and the amount of ethane added ranges from 80 vol. % to 15 vol. % with corresponding ranges of inert diluent added to the ODH process ranging from 0 to 65 vol %. Within these ranges the relative volumetric oxygen:ethane ratio ranges from 0.25 to about 1.33.

In some embodiments the amount of inert diluent added to the ODH process is from about 40 vol. % to about 55 vol. % and the oxygen:ethane ratio is about 0.30.

The effect of altering relative volumetric oxygen:ethane ratio added to the ODH process on carbon dioxide output, measured as carbon dioxide selectivity, can be a change in carbon dioxide selectivity of up to 5 wt. %. In some embodiments, the change in carbon dioxide selectivity is about 2.5 wt. %. In other embodiments, the change in carbon dioxide selectivity is about 1.0 wt. %.

Carbon Dioxide Negative

An aspect of the present invention is the ability of an operator to tailor conditions to promote oxidation of carbon dioxide so that the overall process is either carbon dioxide neutral or even carbon dioxide negative. By including carbon dioxide as or part of the inert diluent a net carbon dioxide negative process can be followed. This would allow using captured carbon dioxide from a process that produces carbon dioxide, minimizing the need to flare or convert the captured carbon dioxide. For example, a process of ODH of ethane results in a product stream that includes unreacted ethane, ethylene, water and one or more of carbon dioxide, acetic acid, and carbon monoxide. The wide variety of products necessitates separation downstream of the reactor. Acetic acid and water are removed using a quench tower, while carbon dioxide can be removed via a combination of an amine wash tower and a caustic tower. The remaining ethane and ethylene can be separated using a splitter so that the ethane can be recycled to the ODH reactor and the relatively pure ethylene can be used in downstream applications, most notably polymerization using any known catalyst to make polyethylene. For example, the ethylene produced can be used to make low density polyethylene (LDPE), linear low density polyethylene (LLDPE), high density polyethylene (HDPE), and the lowest density products, elastomers and plastomers using methods known in the art.

The carbon dioxide removed by the amine wash tower would normally be flared off, contributing to the emission of greenhouse gases. In the present disclosure, the carbon dioxide can be used as inert diluent in the ODH process where the amount of steam added and relative volumetric oxygen:ethane ratio added are adjusted accordingly to promote oxidation of the carbon dioxide added. In some embodiments captured carbon dioxide from an ODH process separation train is used as inert diluent and the amount of steam added to the ODH process is adjusted so that carbon dioxide output is neutral or negative. A person skilled in the art would appreciate that operating under carbon dioxide negative conditions cannot continue endlessly without external supply of carbon dioxide. As the supply of captured carbon dioxide approaches zero the operator can reduce the amount of steam added under the ODH process is carbon dioxide neutral.

In some embodiments, the present disclosure contemplates a continual carbon dioxide negative process where carbon dioxide is supplied from an industrial process, such as thermal cracking. In this instance, the opportunity exists for reducing the amount of carbon dioxide that must be flared under normal operating conditions for the industrial process. In this embodiment, the operator maximizes the amount of steam added to the reaction and the relative volumetric oxygen:ethane ratio added to the reactor to decrease carbon dioxide selectivity so that added carbon dioxide added from an industrial process is almost entirely consumed.

EXAMPLES

Example 1

The effect of altering the amount of steam injected into an ODH process on the carbon dioxide output was assessed using two fixed bed reactors, connected in series. The catalyst present in each of the reactors was a mixture of several batches of a mixed metal oxide catalyst of the formula: $Mo_{1.0}V_{0.30-0.50}Te_{0.10-0.20}Nb_{0.10-0.20}O_d$, where the subscripts represent the range of atomic amounts of each element, relative to Mo, present in the individual batches, and d represents the highest oxidation state of the metal oxides present in the catalyst. The catalyst was extruded with 6.8 wt. % of $TiO_2$. Furthermore, the catalyst was diluted physically with Denstone® 99 Alumina powder with weight ratio of catalyst to diluent of 2.1. Denstone® 99 Alumina consists mainly (99 wt. %) of alpha structure $Al_2O_3$. Ethane, carbon dioxide, and oxygen were premixed before addition of water, followed by preheating with the entire composition being fed to the first of the two reactors. The preheating step is necessary to ensure the water added is converted to steam before injection into the reactor. Output from the first reactor was sent directly into the second reactor without addition of new reactants. For each reactor, the temperature was held in the range of 334 to 338° C. at ambient pressure. The process was run continuously over a period of three days.

The relative amounts of ethane, carbon dioxide, and oxygen remained the same while the flow rate of steam added to reactor was altered. The relative amounts of ethane, carbon dioxide, and oxygen added to the first reactor were 33, 54, and 13 respectively. The gas hourly space velocity (GHSV) was kept constant at 610 $h^{-1}$. Flow rates of reaction ethane, carbon dioxide and oxygen were altered accordingly to maintain GHSV at 610 $h^{-1}$ after altering the amount of steam added to reactor.

Steam was added indirectly as water with the ethane, carbon dioxide and oxygen mixture. The amount of water added to the mixture before entering the first reactor was varied, starting with no water and increasing in increments up to a flow rate of 1.0 $cm^3$/min. For each flow rate of water added to the mixture, a corresponding weight % of steam in the total feed mixture was calculated. Table 1 shows the effect that changing the amount of steam added to the reactor had on output of carbon dioxide, carbon monoxide, and acetic acid.

Results listed in Table 1 are averaged from two or more experimental runs at each of the prescribed conditions. The results show that increasing the flow rate of water added to the mixture and corresponding increase in the weight % of steam added to the reactor leads to a decrease in the carbon dioxide selectivity. A carbon dioxide negative process was seen when the water was added at a flow rate of 1.0 $cm^3$/min (Example 1-5), which corresponds to 39 weight % of steam added. Also, reverting back to no steam added (Example 1-6) followed by increasing to 39 weight % (Example 1-7) resulted in the carbon dioxide selectivity going positive back to negative. Table 1 reveals that changes in carbon dioxide selectivity are more pronounced when the levels of steam added, when reactor temperature is below 340° C., is changed from below 20% to 35 wt. % up to the maximum of 40 wt. %.

Finally, it should be noted that increasing the steam results in a higher production of acetic acid and also is accompanied by a higher conversion rate of ethane.

TABLE 1

Normalized product selectivity of ODH products in response to
changes in steam added to the reactor.
Temp-334-338° C.; GHSV-610 h$^{-1}$; Vol ratio O$_2$:C$_2$H$_6$-0.4

| Experiment number | Water (not steam) added (cm$^3$/min) | Steam added (wt. %) | Ethane conversion (%) | Product Selectivity (wt %) | | | |
|---|---|---|---|---|---|---|---|
| | | | | C$_2$H$_4$ | CO$_2$ | CO | CH$_3$COOH |
| 1-1 | 0.0 | 0 | 38.4 | 83.0 | 6.30 | 8.1 | 2.6 |
| 1-2 | 0.1 | 3 | 41.6 | 82.0 | 6.0 | 7.7 | 4.3 |
| 1-3 | 0.4 | 13 | 43.5 | 79.2 | 6.0 | 7.0 | 7.7 |
| 1-4 | 0.8 | 29 | 45.8 | 79.2 | 3.6 | 6.8 | 10.4 |
| 1-5 | 1.0 | 39 | 49.8 | 88.7 | −9.8 | 7.3 | 13.8 |
| 1-6 | 0.0 | 0 | 37.9 | 84.2 | 4.4 | 7.8 | 3.7 |
| 1-7 | 1.0 | 39 | 50.0 | 90.4 | −10.5 | 7.3 | 12.8 |

Example 2

A second experiment was conducted using the same reactor configuration from Example 1 but under different operating conditions. The catalyst was a mix of several batches as described for Example 1, and for comparison included a freshly mixed catalyst and a mixed catalyst 8 months after being used intermittently. The relative volumetric amounts of ethane, carbon dioxide, and oxygen added to the first reactor were 42, 37, and 21 respectively. Note the higher volumetric feed ratio of O$_2$/C$_2$H$_6$ compared to Example 1. Also, the gas hourly space velocity (GHSV) was higher, and kept constant at 1015 h$^{-1}$, with reaction temperature being held from between 321 to 325° C. Similar to Example 1 flow rates of ethane, carbon dioxide and oxygen were altered accordingly to maintain GHSV at 1015 h$^{-1}$ after altering the amount of water added. The corresponding steam content added to the first reactor was changed from 0 wt. % to 16 wt. %.

The results of Example 2 are shown in Table 2. As the catalyst ages, selectivity towards the production of by-products, most notably CO$_2$, generally increases, with a concomitant decrease in ethylene selectivity. This can be seen by comparing experiment 2-1 with experiment 2-2, where experiment 2-1 corresponds to the fresh catalyst and experiment 2-2 corresponds to the 8 month old catalyst. Originally, the catalyst showed 91% selectivity to C$_2$H$_6$ and a negative CO$_2$ selectivity of −1.0. After 8 months, selectivity to C$_2$H$_6$ dropped to 89% and CO$_2$ selectivity moved into positive territory at 5.0. Experiment 2 shows that the present invention is also effective with an older catalyst, as increasing weight % of steam added to reactor from 0 to 16 weight % results in a drop in CO$_2$ selectivity to 3.0 from 5.0 (Experiment 2-3). This decrease is in good agreement with the observed trend in Example 1.

TABLE 2

Normalized product selectivity of ODH products using
higher feed ratio of O$_2$/C$_2$H$_6$ and with fresh versus used catalyst.
Temp-321-325° C.; GHSV-1015 h$^{-1}$; Vol ratio O$_2$:C$_2$H$_6$-0.5

| Experiment number | Water (not steam) added (cm$^3$/min) | Steam added (wt. %) | Ethane conversion (%) | Product Selectivity (wt %) | | | |
|---|---|---|---|---|---|---|---|
| | | | | C$_2$H$_4$ | CO$_2$ | CO | CH$_3$COOH |
| 2-1 (fresh) | 0.0 | 0 | 31.0 | 91.0 | −1.0 | 5.0 | 5.0 |
| 2-2 (used) | 0.0 | 0 | 26.0 | 89.0 | 5.0 | 4.0 | 3.0 |
| 2-3 (used) | 0.97 | 16 | 35.0 | 87.0 | 3.0 | 4.0 | 5.0 |

Example 3

A third experiment was conducted using the same reactor configuration as the previous examples, but only using the second reactor in the series and under variable feed volume ratios of oxygen to ethane. The catalyst used was a mixed metal oxide catalyst of the formula: Mo$_{1.0}$V$_{0.37}$Te$_{0.23}$Nb$_{0.14}$O$_{4.97}$ and was extruded with ~55 wt. % of Versal 250 in balance mixed metal oxide. Three relative volumetric amounts of oxygen and ethane were tested, including 16 vol % O$_2$: 38 vol % C$_2$H$_6$, 19 vol % O$_2$: 36 vol % C$_2$H$_6$, and 21 vol % O$_2$: 33 vol % C$_2$H$_6$, which correspond to O$_2$:C$_2$H$_6$ volumetric ratios of 0.4, 0.5, and 0.6, respectively. The relative volumetric amount of CO$_2$ added was maintained at 46 vol %, the gas hourly space velocity (GHSV) was kept constant at 1111 h$^{-1}$, the reaction temperature was held between 359° C. and 360° C., and reactions were performed at ambient pressure. No steam was added to the reaction.

The results of Example 3 are shown in Table 3. As the volumetric ratio of oxygen:ethane is increased the selectivity towards the production of CO$_2$ decreases. This effect is accompanied by slight increases to selectivity towards ethylene and carbon monoxide, while acetic acid selectivity remains unchanged. Experiment 3 demonstrates that altering volumetric ratio of oxygen:ethane added to the reactor, while keeping other parameters unchanged, can decrease the selectivity to carbon dioxide. This effect is also demonstrated by comparing Examples 1 and 2, specifically experiment numbers 1-1 and 2-1 where no steam was added, in that the carbon selectivity was lower in experiment number 2-1 where a higher volumetric ratio of oxygen:ethane was added to the reactor.

TABLE 3

Normalized product selectivity of ODH products in response to variations of volumetric feed ratio of $O_2/C_2H_6$ at elevated temperature and without the addition of steam.
Temp-359-360° C.; GHSV-1110 h$^{-1}$; Steam added-0 vol %

| Experiment number | Volumetric feed ratio $O_2:C_2H_6$ | Steam added (wt %) | Ethane conversion (%) | Product Selectivity (wt %) | | | |
|---|---|---|---|---|---|---|---|
| | | | | $C_2H_4$ | $CO_2$ | CO | $CH_3COOH$ |
| 3-1 | 0.4 | 0 | 48.0 | 83.5 | 7.0 | 6.4 | 3.1 |
| 3-2 | 0.5 | 0 | 49.0 | 84.1 | 6.0 | 7.1 | 2.9 |
| 3-3 | 0.6 | 0 | 47.0 | 86.4 | 2.1 | 8.2 | 3.3 |

Example 4

A fourth experiment was conducted using the same reactor configuration as the previous examples and similar to example 1 but using a higher volumetric ratio of oxygen: ethane (0.5) added to the reactor, a higher GHSV (1111 h$^{-1}$), and a higher temperature of 360° C. The weight % of steam added to the reactor was changed from 0 wt. % to 40 wt. %, while keeping the relative volumetric amount of $CO_2$ steam added (46 vol %) constant. The results are presented in Table 4 and demonstrate that at higher temperatures, flow rates and volumetric ratio of oxygen:ethane increasing the amount of steam added to the reactor from 0 wt. % to 40 wt. % decreases the $CO_2$ selectivity. In this example, the $CO_2$ selectivity decreased from 6.0 wt. % to 5.3%. This decrease is lower than what is seen when operating at a lower temperature, low flow rate (GHSV), and lower relative volumetric ratio of oxygen:ethane added to the reactor.

TABLE 4

Normalized product selectivity of ODH products in response to changes in steam added to the reactor at higher temp., GHSV, and vol. ratio $O_2$:ethane.
Temp-360° C.; GHSV-1111 h$^{-1}$; Vol ratio $O_2:C_2H_6$-0.5

| Experiment Number | Steam added (wt. %) | Ethane conversion (wt %) | Product Selectivity (wt %) | | | |
|---|---|---|---|---|---|---|
| | | | $C_2H_4$ | $CO_2$ | CO | $CH_3COOH$ |
| 4-1 | 0 | 49 | 84.1 | 6.0 | 7.1 | 2.9 |
| 4-2 | 40 | 49 | 78.4 | 5.3 | 7.1 | 9.2 |

The invention claimed is:

1. A method for controlling the carbon dioxide output from an oxidative dehydrogenation process comprising the steps of:
   i) introducing a gas mixture comprising ethane and oxygen, and optionally one or more of steam and inert diluent, into at least one ODH reactor containing an ODH catalyst, provided that if more than one ODH reactor is present then each reactor may contain the same or different ODH catalyst and at least one of the ODH catalysts is capable of utilizing carbon dioxide as an oxidizing agent, under conditions to produce a product stream from the at least one ODH reactor comprising ethylene, and optionally one or more of unreacted ethane, unreacted oxygen, carbon dioxide, carbon monoxide, inert diluent, and acetic acid;
   ii) measuring a carbon dioxide level in the product streams; and
   either:
   a. introducing steam, or increasing an amount of steam introduced, into the at least one ODH reactor in an amount sufficient to decrease carbon dioxide levels if the measured carbon dioxide level is above a predetermined target carbon dioxide level;
   b. decreasing the flow rate of steam introduced into the at least one ODH reactor to increase the carbon dioxide level if steam was introduced in step i) and the measured carbon dioxide level is below a predetermined target carbon dioxide level;
   c. increasing the volumetric ratio of oxygen to ethane in the gas mixture introduced into the at least one ODH reactor to a degree sufficient to decrease the carbon dioxide level if the measured carbon dioxide level is above a predetermined target carbon dioxide level; or
   d. decreasing the volumetric ratio of oxygen to ethane in the gas mixture introduced into the at least one ODH reactor to a degree sufficient to increase the carbon dioxide level if the measured carbon dioxide level is below a predetermined target carbon dioxide level.

2. The method of claim 1 wherein one of the at least one ODH reactors is a fixed bed reactor.

3. The method of claim 2 wherein the at least one fixed bed ODH reactor comprises heat dissipative particles having a thermal conductivity greater that the catalyst.

4. The method of claim 1 wherein one of the at least one ODH reactors is a fluidized bed reactor.

5. The method of claim 1 wherein at least one of the ODH catalysts is a mixed metal oxide.

6. The method of claim 1 wherein at least one of the ODH catalysts comprises a mixed metal oxide of the formula:

wherein a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to satisfy the valence state of the catalyst.

7. The method of claim 1 wherein steam comprises up to 60 wt. % of the gas mixture.

8. The method of claim 1 wherein the conditions in one of the at least one ODH reactors include temperatures from 300° C. to 450° C., pressures from 0.5 to 150 psig, and a residence time of the ethane in the at least one ODH-reactor from 0.002 to 30 seconds.

9. The method of claim 1 wherein the gas mixture has a gas hourly space velocity of from 500 to 30000 $h^{-1}$.

10. The method of claim 1 wherein the gas mixture has a weight hourly space velocity of from 0.5 $h^{-1}$ to 50 $h^{-1}$.

11. The method of claim 1 wherein the gas mixture has a linear velocity of from 5 cm/sec to 1500 cm/sec.

12. The method of claim 1 wherein the at least one ODH reactor is maintained at a temperature below about 340° C.

13. The method of claim 12 wherein an initial amount of steam that was added into the at least one ODH reactor ranges from 0 wt. % to about 20 wt. % and the method further comprising increasing the amount of steam to a range from about 35 wt. % to about 60 wt. % to provide an absolute decrease in the carbon dioxide level, measured as normalized product selectivity, of from 2.5 wt. % to 15 wt. %, wherein each wt. % is based on the weight of total feed into the at least one ODH reactor.

14. The method of claim 12 wherein steam added into the at least one ODH reactor is from about 35 wt. % to about 60 wt. % and is decreased to from about 0 wt. % to about 20 wt. % and results in an absolute increase in the carbon dioxide level, measured as normalized product selectivity, of from 2.5 wt. % to 15 wt. %, wherein each wt. % is based on the weight of total feed into the at least one ODH reactor.

15. The method of claim 1 wherein the at least one ODH reactor is maintained at a temperature above about 350° C.

16. The method of claim 15 wherein an initial amount of steam that was added into the at least one ODH reactor ranged from 0 wt. % to about 10 wt. % and the method further comprising increasing the amount of steam to a range from about 40 wt. % to about 60 wt. % to provide an absolute decrease in the carbon dioxide level, measured as normalized product selectivity, of at least 0.5 wt. %, wherein each wt. % is based on the weight of total feed into the at least one ODH reactor.

17. The method of claim 15 wherein steam added into the at least one ODH reactor is from about 40 wt. % to about 60 wt. % and decreased to from about 0 wt % to about 10 wt. % and results in an absolute increase in the carbon dioxide level, measured as normalized product selectivity, of at least 0.5 wt. %, wherein each wt. % is based on the weight of total feed into the at least one ODH reactor.

18. The method of claim 1 wherein the vol % of oxygen in the gas mixture is about 20%, and the volumetric ratio of oxygen:ethane in the gas mixture is about 0.4 and is changed to a volumetric ratio of oxygen:ethane to about 0.6 and results in an absolute decrease in the carbon dioxide level, measured as normalized product selectivity, of at least 2.5 wt. %.

19. The method of claim 1 wherein the vol % of oxygen in the gas mixture is such that the gas mixture stays outside of the flammable envelop of the gas mixture, and the volumetric ratio of oxygen:ethane in the gas mixture is about 0.1 and is changed to the maximum ratio allowed before the gas mixture enters the flammable envelop of the gas mixture and results in an absolute change in the carbon dioxide level, measured as normalized product selectivity, of at least 0.5 wt. %.

* * * * *